(12) United States Patent
Lu et al.

(10) Patent No.: US 9,408,636 B2
(45) Date of Patent: Aug. 9, 2016

(54) BONE CONNECTION MATERIAL

(71) Applicants: Luke Lu, San Diego, CA (US);
Toshihiro Tokizawa, Tokyo (JP);
Kuan-Yu Lu, Taipei (TW); I-Ching Lu,
Taipei (TW)

(72) Inventors: Luke Lu, San Diego, CA (US);
Toshihiro Tokizawa, Tokyo (JP);
Kuan-Yu Lu, Taipei (TW); I-Ching Lu,
Taipei (TW)

( * ) Notice: Subject to any disclaimer, the term of this patent is extended or adjusted under 35 U.S.C. 154(b) by 0 days.

(21) Appl. No.: 14/607,088

(22) Filed: Jan. 28, 2015

(65) Prior Publication Data

US 2015/0209095 A1    Jul. 30, 2015

Related U.S. Application Data

(63) Continuation-in-part of application No. 14/164,258, filed on Jan. 27, 2014.

(51) Int. Cl.
| | | |
|---|---|---|
| A61B 17/68 | (2006.01) | |
| A61B 17/86 | (2006.01) | |
| A61B 17/80 | (2006.01) | |
| A61L 31/02 | (2006.01) | |
| A61L 31/08 | (2006.01) | |
| A61L 31/04 | (2006.01) | |
| A61F 2/28 | (2006.01) | |
| A61B 17/70 | (2006.01) | |
| A61L 31/18 | (2006.01) | |
| A61L 31/16 | (2006.01) | |

(52) U.S. Cl.
CPC ............. *A61B 17/68* (2013.01); *A61B 17/7002* (2013.01); *A61B 17/80* (2013.01); *A61B 17/866* (2013.01); *A61F 2/28* (2013.01); *A61L 31/026* (2013.01); *A61L 31/028* (2013.01); *A61L 31/044* (2013.01); *A61L 31/086* (2013.01); *A61L 31/16* (2013.01); *A61L 31/18* (2013.01); *A61L 2430/02* (2013.01)

(58) Field of Classification Search
CPC .. A61B 17/7002; A61B 17/80; A61B 17/866; A61F 2/28; A61L 31/026; A61L 31/028; A61L 31/044; A61L 31/086; A61L 31/16; A61L 2430/02
See application file for complete search history.

(56) References Cited

U.S. PATENT DOCUMENTS

| | | | | |
|---|---|---|---|---|
| 5,674,286 A | * | 10/1997 | D'Alessio | A61B 17/80 424/423 |
| 5,733,326 A | * | 3/1998 | Tomonto | A61L 27/04 623/1.44 |
| 2005/0136764 A1 | * | 6/2005 | Sherman | A61B 17/7059 442/103 |

* cited by examiner

*Primary Examiner* — Larry E Waggle, Jr.
(74) *Attorney, Agent, or Firm* — Leong C. Lei

(57) ABSTRACT

The present invention provides a bone connection material that includes an internal layer. The internal layer is formed by braiding a plurality of filaments. The internal layer that is formed by braiding filaments is resistant to lateral shearing forces and may provide flexibility so as to achieve wide applications. Further, the present invention overcomes the drawback of the conventionally used metallic materials that are rigid and inelastic and also overcomes the problem of polylactic acid material of being brittle. Thus, the bone formed according to the present invention is close to a natural bone and is more suitable for uses in portions where frequent movements are made and scaffolds of stem cells.

14 Claims, 18 Drawing Sheets

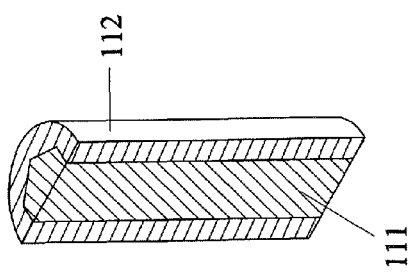
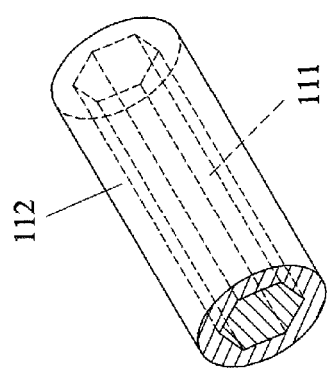
FIG. 12

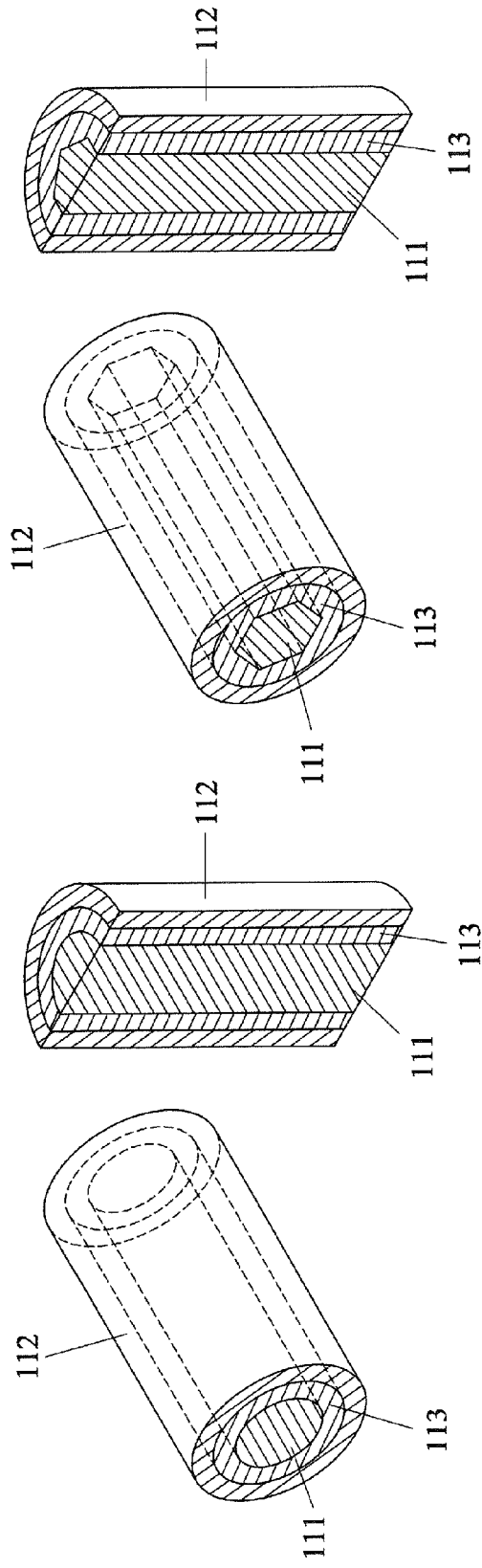

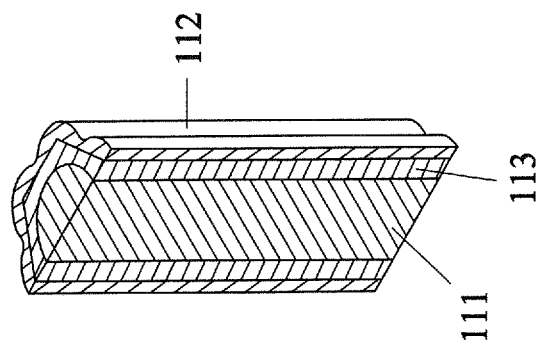
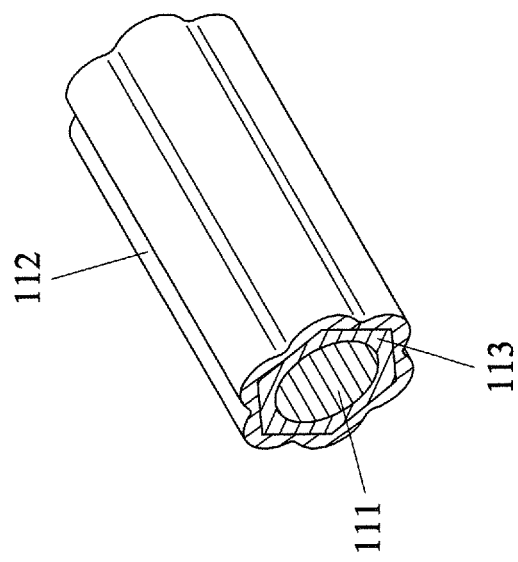
FIG. 17

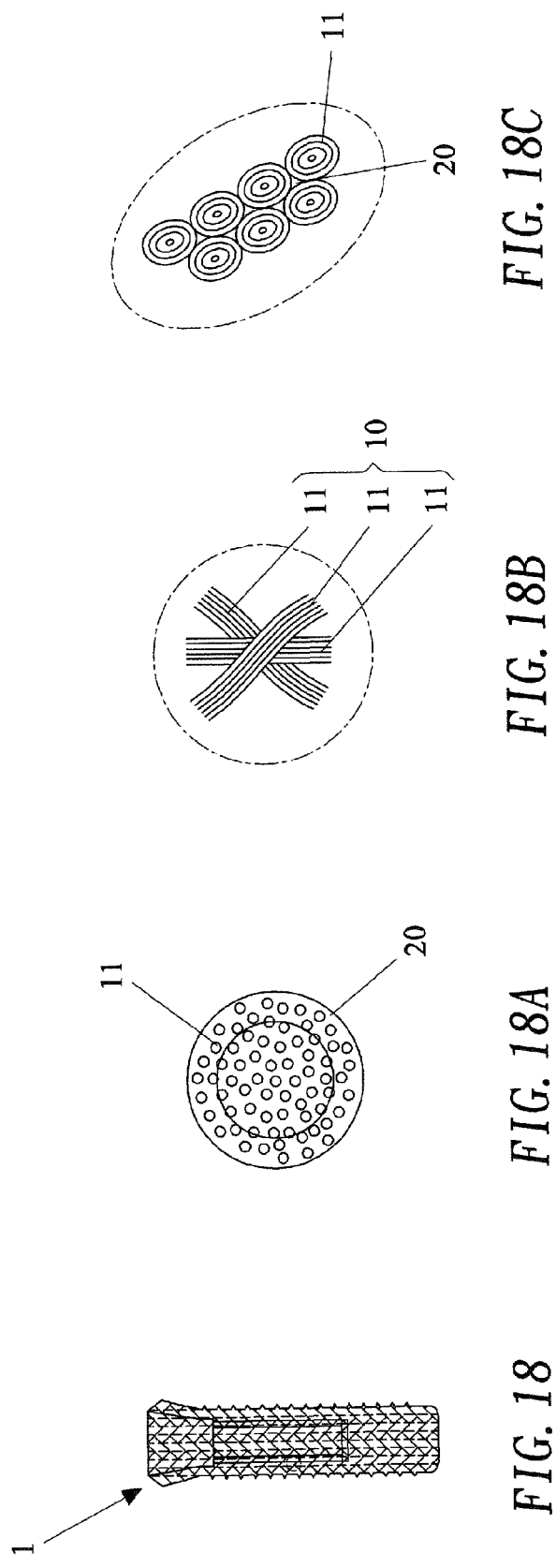

BONE CONNECTION MATERIAL

CROSS-REFERENCE TO RELATED APPLICATION

This is a continuation-in-part of co-pending U.S. patent application Ser. No. 14/164,258 filed on Jan. 27, 2014 and owned by the present applicant.

(a) TECHNICAL FIELD OF THE INVENTION

The present invention generally relates to a bone connection material and a manufacturing method thereof, and more particularly to a bone connection material that is made by braiding fiber filaments and resin matrix.

(b) DESCRIPTION OF THE PRIOR ART

In the surgical operations, bone screws and bone plates are commonly used as a connection member for connecting teeth bone, cranial bones, facial and limb fractures. When the patient's body makes movements, the nail screws and nail bones that serves the connection members may induce stresses, so that materials, such as titanium and steel, are commonly used to make bone screws and bone plates.

Further, when the bone screws and bone plates that are made of titanium or steel are placed in the bone connection of a patient, due to the natures of the materials that are rigid and inelastic, it often results in obstruction to the movements of the joint. Further, a bone connection material screw made of polylactic acid and hydroxylapatite is also available, but it has a disadvantage of being brittle in nature so that it may get cracking when subjected to an external force. It only works as an ancillary connection material for positioning purpose and is not fit for portions where frequent movements are made.

In light of the above, the present invention aims to provide a solution that overcomes the drawbacks.

SUMMARY OF THE INVENTION

In view of the above-discussed problems, the present invention aims to provide a bone connection material that comprises an internal layer. The internal layer is formed by braiding a plurality of filaments. The internal layer that is formed by braiding filaments is resistant to lateral shearing forces and may provide flexibility so as to achieve wide applications, and is fitter for portions where frequency movements are made than the conventionally used material of steel, and in addition, is not so inclined to be rejected by human body as the conventionally used metallic material.

Further, the present invention may further comprise a covering layer. The covering layer is arranged to enclose the filaments of the internal layer.

Preferably, the covering layer is made of a thermoplastic resin or a thermosetting resin or any biocompatible resin to improve elasticity.

Preferably, the covering layer further comprises collagen, screws made of polylactic acid, or hydroxylapatite. Interaction induced between these materials and inner tissues may help to increase the speed of growth and restoration of bones.

Preferably, the filaments are bioactive glass fibers, bioactive materials, or bioinert glass fibers, or bioinert materials, which are selected according to the site and property of the bone connection material used and can be manufactured to show a desired outer configuration so as to provide far superior capability of promoting bone healing to the prior art.

Preferably, the inner layer is made in the form of a bone screw, a bone plate, or bone rod, to suit the need of use of the contemporary technology.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

BRIEF DESCRIPTION OF THE DRAWINGS

FIG. 12 is illustrating schematic diagram of a single filament used in the bone connection material according to an embodiment of the present invention.

FIGS. 15A and 15B are illustrating schematic diagrams of a single filament used in the bone connection material according to the embodiments of the present invention.

FIG. 17 is illustrating schematic diagram of a single filament used in the bone connection material according to an embodiment of the present invention.

FIG. 18 is illustrating schematic diagram of a bone connection material according to another general embodiment of the present invention.

FIG. 18A shows an enlarged top view of FIG. 18.

FIG. 18B shows a woven filament structure of FIG. 18.

FIG. 18C shows a section-enlarged view of the woven filament structure of FIG. 18B.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

The embodiments of the present invention are a bone connection material. To make those skilled in the art to undoubtedly understand the embodiments, the structures of the bone connection materials will be described first. The materials and types of filaments that are used in the embodiments will then be discussed.

Figure 1:
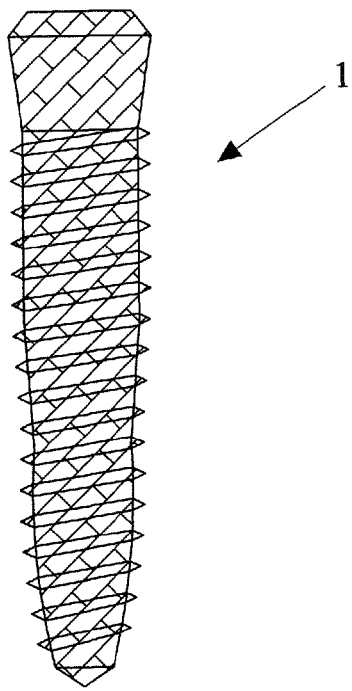
FIG. 1 shows a side elevational view of an embodiment of the present invention that is made by being braided as a screw.
Figure 1A:
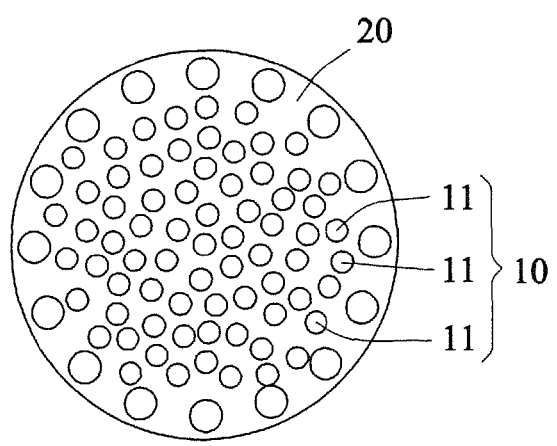
FIG. 1A shows an enlarged top view of FIG. 1.

Referring to FIG. 1 and FIG. 1A, a bone connection material 1 according to an embodiment of the present invention is show, which comprises an internal layer 10 and a covering layer 20. The internal layer 10 is made by braiding a plurality of filaments 11 to show in a predetermined form that corresponds to a desired bone connection material. The covering layer 20 encloses the filaments 11 of the internal layer 10. The plurality of filaments 11, after being braided properly, results in a combination of the strength of all the filaments to thereby provide a material that is resistant to fracture and shows flexibility, making it suitable for connection of bones or serving as a framework of stem cells. In an actual operation, it is possible to solely form the internal layer 10 through braiding the filaments and the internal layer 10 is thus made in the form of a bone connection material.

Figure 8:
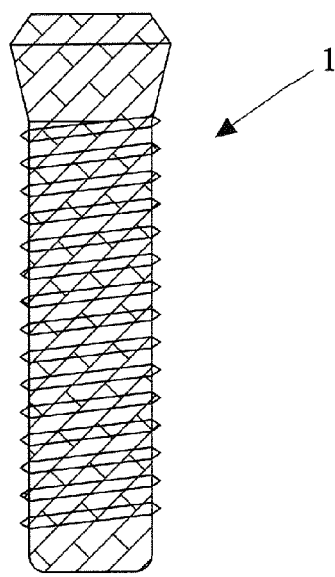
FIG. 8 shows an embodiment of the present invention that is made by being braided as a screw.
Figure 8A:
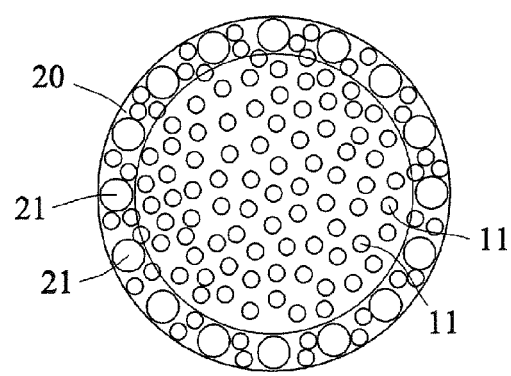
FIG. 8A shows an enlarged top view of FIG. 8.

Further, an arrangement of the covering layer 20 may be additionally included so as to make the application of the bone connection material wide. The covering layer 20 is made of a thermoplastic resin, a thermosetting resin, biocompatible polymer or a biodegradable resin and matrix collagen, hydroxylapatite (HA), or may further include other additives 21, as shown in FIG. 8 and FIG. 8A, such as collagen, hydroxylapatite (HA), or tricalcium phosphate (TCP). HA is a major constituent of human bone tissues and once implanted in human bodies, may release calcium and phosphorus that may be absorbed by body tissues to grow new tissues. Generally, the human body will itself generate HA or related or similar elements for proceeding with reconstruction of bones, but the time it may take is dependent on the individual body. The covering layer provided by the present invention is provided to contain such bone reconstruction materials so as to be used for body reconstruction and to provide an effect of accelerated restoration.

Further, the filaments 11 can be bioactive glass fibers, ceramic fiber materials, bioactive materials, or bioinert glass fiber materials, which can be used and arranged corresponding to the needs of the actual situations.

Figure 2:
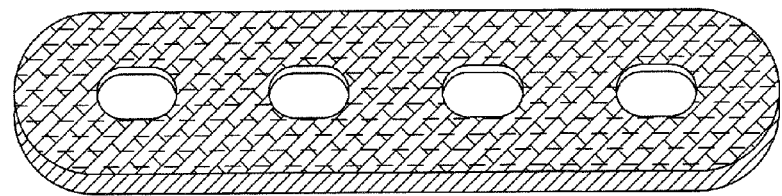
FIG. 2 shows a perspective view of an embodiment of the present invention that is made by being braided as a bone connection plate.
Figure 3:
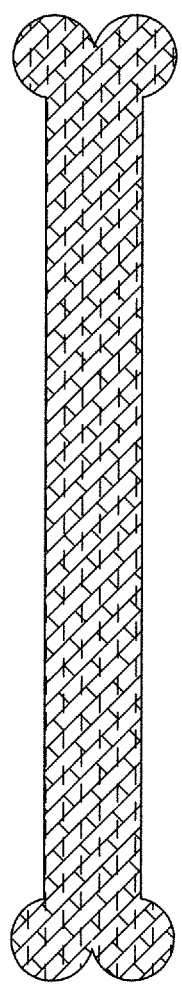
FIG. 3 shows a plan view of an embodiment of the present invention that is made by being braided as a bone or pipe bone shape.
Figure 4:
FIG. 4 shows a plan view of an embodiment of the present invention that is made by being braided as a bar, rod or pipe shape.
Figure 5:
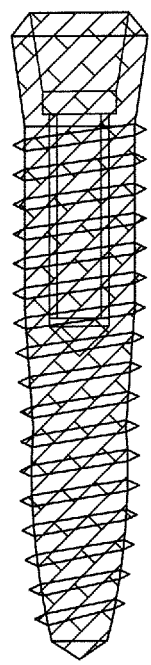
FIG. 5 shows a side elevational view of an embodiment of the present invention that is made by being braided as a screw having an internal thread.
Figure 6:
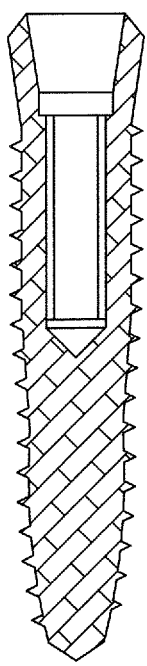
FIG. 6 shows a cross-sectional view of the embodiment of the present invention that is made by being braided as a screw having an internal thread.
Figure 7:
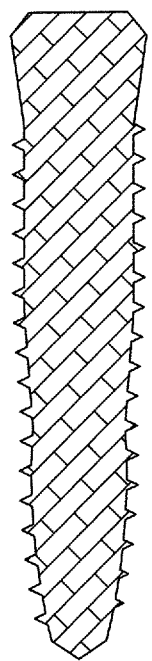
FIG. 7 shows a cross-sectional view of an embodiment of the present invention that is made by being braided as a screw.

Further, the internal layer 10 can be made in the form of a bone screw as shown in FIG. 1 or bone plates (for connection) shown in FIGS. 2-4 or bone screws shown in FIGS. 5-7. These are known configurations of the prior art devices and are examples that can be embodied in the present invention. It is apparent that these types of devices, such as bone screws, bone connection plates/blocks, and tooth root implants, can be made according to the embodiments of the present invention through braiding. Further, braiding can be achieved through various processes. For example, one of the braiding processes is that one of the filaments is taken as a main axis, around which the other filaments are arranged to wrap. An alternative braiding process is that two or three filaments are arranged to inter-entangle and interlacing each other to show a twist form. A further alternative braiding process is that secondary braiding is applied to filaments that have already braided together so that the braided filaments are braided again with other braided or non-braided filaments. These are only illustrative examples of braiding that can be used in the embodiments of the present invention and a variety of other braiding processes that can be used and are not described fully herein are also considered within the scope of "braiding" defined in the present invention.

Figure 9:
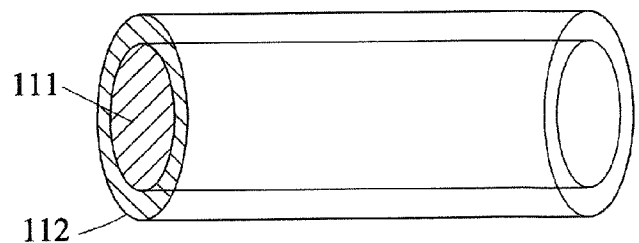
FIG. 9 shows a perspective view of a multilayer single filament of an embodiment of the present invention.
Figure 10:
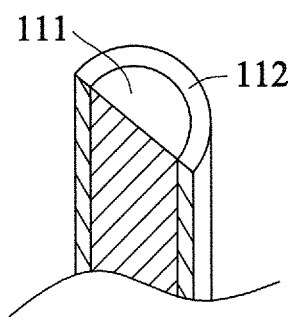
FIG. 10 shows a cross-sectional view of the multilayer single filament of the embodiment of the present invention.

The structure shown in FIGS. 9 and 10 can be adopted, which is a multilayer single filament. This type of filament comprises a core layer 111 and a shell layer 112. The core layer 111 is made of an X-ray opacity bioinert material. The shell layer 112 is arranged to enclose a circumferential surface of the core layer 111 and is made of a bioactive glass fiber material, a bioactive ceramic fiber material, HA, or TCP. All these described here are examples of filaments that can be used in the present invention. For a bone connection material made of the multilayer structure and material, the shell layer 112 can help bones to grow and can be retained in human body without causing undesired influence, so that there is no need for them to be removed through surgical operations. Further, they are not made of titanium or steel so that they do not cause allergic response of human body. The conventional bone connection material cannot be long retained in human body so that when the patient has healed to quite an extent, a secondary operation must be taken a surgeon on the patient to take out the connection members. This leads to additional risks of anesthesia and postoperative infection caused by the secondary operation. This causes economic, physiologic, and mental burden for the patient. Bioactive glasses are promising scaffold materials for bone regeneration because of their ability to convert to hydroxyapatite (HA), the main mineral constituent of bone, as well as their proven osteoconductivity and their ability to form a strong bone with hard tissues and soft tissues.

Figure 11B:
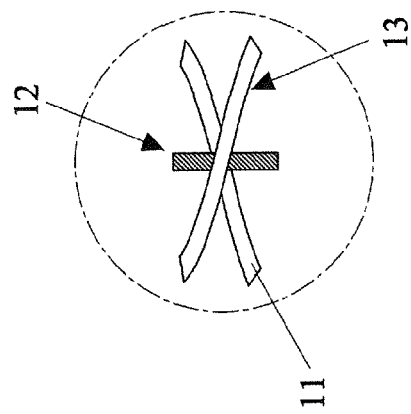
FIG. 11B shows a woven filament structure of FIG. 11.
Figure 11A:
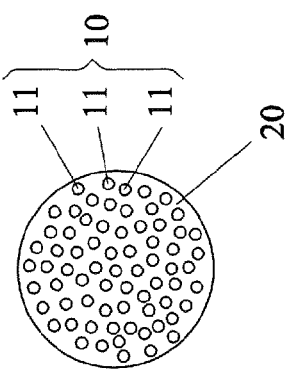
FIG. 11A shows an enlarged top view of FIG. 11.
Figure 11:
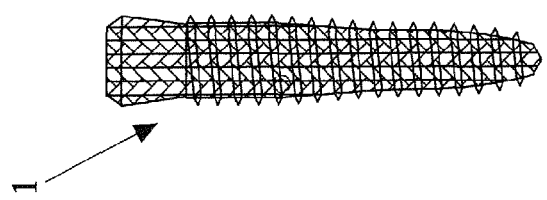
FIG. 11 is illustrating schematic diagram of a bone connection material according to a general embodiment of the present invention.

Please refer to FIG. 11, which illustrating schematic diagram of a bone connection material 1 according to a general embodiment of the present invention. Please refer to FIG. 11A, which illustrating a top view of the bone connection material 1. In FIG. 11A, it can be seen that filaments 11 are fixed within the covering layer 20 and thus are provided within the bone connection material 1. Continue to refer to FIG. 11B, it can be seen that filaments 11 are braided to form a woven filament structure. The woven filament structure is advantageous for the bone connection material 1 to be able to have high tensile strength and elasticity at the same time.

FIG. 11B shows that the woven filament structure includes a center filament shaft 12 and a plurality of braided filament shafts 13. The center filament shaft 12 is provided straightly through the woven filament structure, while the braided filament shafts 13 are interlaced-knitted around the center filament shaft. This "*" pattern of FIG. 11B provides additional fixation for the braided filament shafts 13 and higher tensile strength in vertical direction and thus more rugged structure is yielded, as comparing to traditional structure with "x" pattern.

The resin of the covering layer 20 may be made of bioinert or biodegradable materials in order to facilitate osseointegration process, and the resin of the covering layer 20 may be thermosetting or thermoplastic, depending on the implementations. A single filament 11 is multilayer filament. Detailed description will be stated in the followings.

Please refer to FIG. 12, which illustrating schematic diagram of a single filament used in the bone connection material 1 according to an embodiment of the present invention. In this embodiment, a single filament 11 of the bone connection material 1 is a multilayer filament, and a plurality of coefficients of thermal expansion of layers of the multilayer filament is equal to each other or gradually lower in order from an inner layer to an outer layer. It can be seen that a single filament used in the bone connection material 1 is two-layer filament. In this embodiment, the multilayer filament includes a core layer 111 and a shell layer 112, the shell layer 112 encloses a circumferential surface of the core layer 111 and has a coefficient of thermal expansion lower than that of the core layer 111. Of course, in other embodiment, the coefficient of thermal expansion of shell layer 112 and that of the core layer 111 are also can be the same. This configuration is advantageous for the two-layer filament to be able to provide higher tensile force, and thus higher tensile strength for the bone connection material 1 can be provided. Each layer of the multilayer filament is formed with a round, a hexagonal, or a strip layer. In this embodiment, the core layer 111 is formed with a round, or a hexagonal layer, while the shell layer 112 is formed with a round layer. At least one layer of the multilayer filament is made of bioinert material, and at least one layer of the multilayer filament is made of bioactive material. The shell layer 112 in this embodiment is made of bioactive materials, such as bioglass, collagen, hydroxylapatite (HA), or tricalcium phosphate (TCP). While the shell layer 112 is in contact with the bone, the bioactive material may be released from the shell layer 112 and thus is in contact with the osteoblast of the bone for osseointegration. The core layer 111 in this embodiment may be made of bioinert material with X ray opacity so as to maintain the structure of bone connection material 1 and to be shown up on the X ray scan.

Figure 13A:
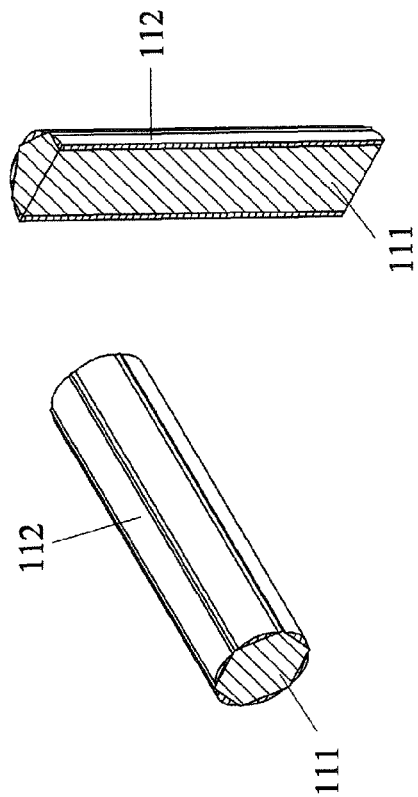
FIGS. 13A and 13B are illustrating schematic diagrams of a single filament used in the bone connection material according to the embodiments of the present invention.
Figure 13B:
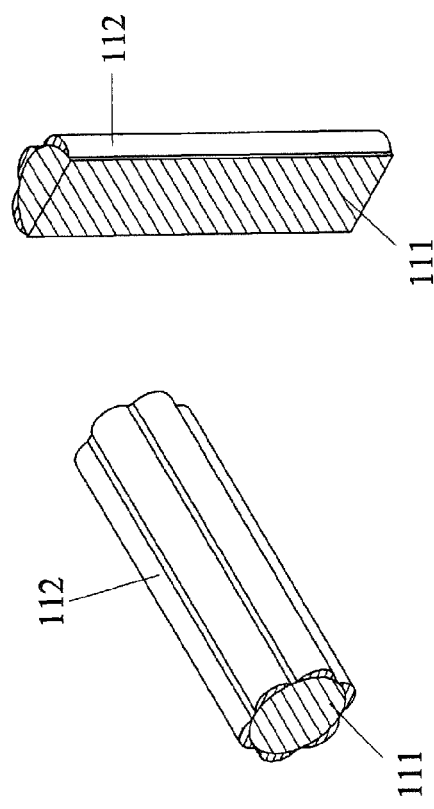
Figures 14A, 14B:
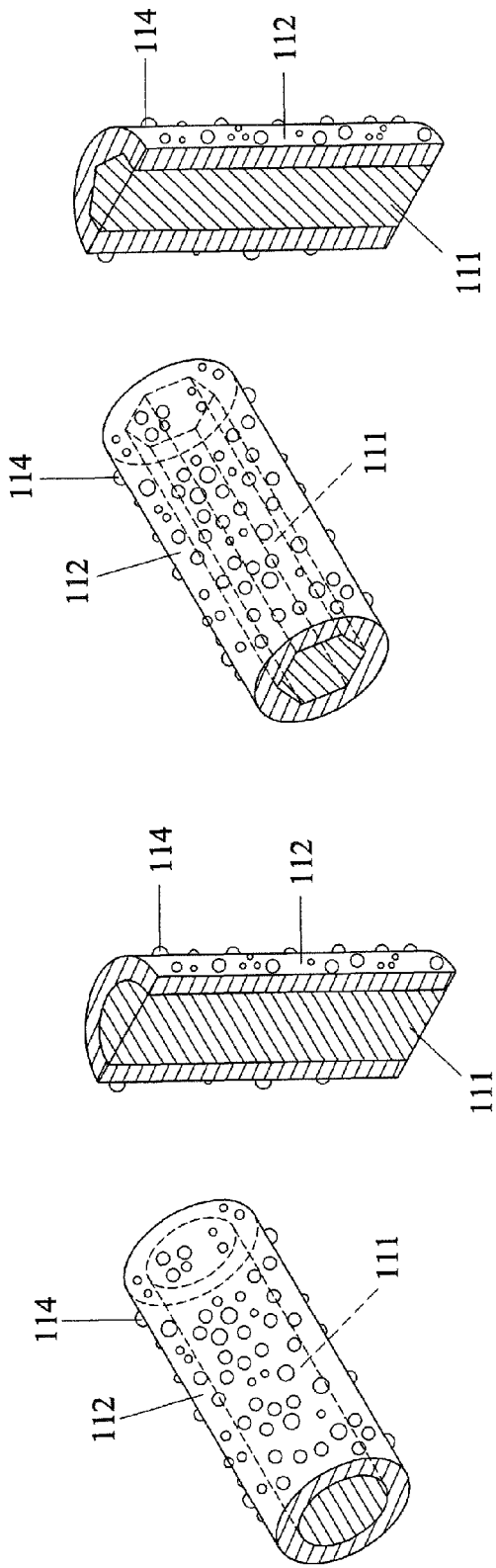
FIGS. 14A and 14B are illustrating schematic diagrams of a single filament used in the bone connection material according to the embodiments of the present invention.

Refer to FIGS. 13A and 13B, which respectively illustrating schematic diagrams of a single filament used in the bone connection material 1 according to the embodiments of the present invention. In these embodiments, the shell layer 112 is formed with a strip layer. The function of strip configuration is to provide more fixation force between filaments. Please refer to FIGS. 14A and 14B, an outer surface of the shell layer 112 has an extra punctate coating 114. The function of punctate coating 114 is also to provide more fixation force and more surface contact area between filaments 11 and between filaments 11 and bone.

Refer to FIGS. 15A and 15B, a single filament used in the bone connection material 1 is three-layer filament. In these embodiments, the multilayer filament includes a core layer 111, a middle layer 113, and a shell layer 112, the middle layer 113 encloses a circumferential surface of the core layer 111, while the shell layer 112 encloses a circumferential surface of the middle layer 113. A coefficient of thermal expansion of the shell layer 112 is lower than a coefficient of thermal expansion of the middle layer 113, and the coefficient of thermal expansion of the middle layer 113 is lower than that of the core layer 111. At least one layer of the multilayer filament is made of material with Xray opacity. At least one layer of the multilayer filament is made of bioinert material, and at least one layer of the multilayer filament is made of bioactive material. In these embodiments, the core layer 111 and/or the middle layer 113 may be made of bioinert glass filament with X ray opacity or bioinert material, while the shell layer 112 is made of bioactive materials, such as bioglass, collagen, hydroxylapatite (HA), or tricalcium phosphate (TCP). The purpose of this three-layer configuration is that when the shell layer 112 osseointegrates with bones, two-layer structure constituted by the remained core layer 111 and middle layer 113 can be still remained. Besides, the three-layer configuration can inherently undertake greater tensile force, as comparing to two-layer configuration. In these embodiments, the core layer 111 may be formed with a round or a hexagonal layer while the middle layer 113 and the shell layer 112 are formed with a round layer. Of course, the present invention is not limited to this, in another embodiment, the core layer 111 and/or the middle layer 113 is made of bioactive materials, such as bioglass, collagen, hydroxylapatite (HA), or tricalcium phosphate (TCP), and the shell layer 112 may be made of bioinert glass filament with X ray opacity or bioinert material. Therefore, the bioactive material may be released from the core layer 111 or the middle layer 113 and thus is in contact with the osteoblast of the bone for osseointegration.

Figures 16A, 16B:
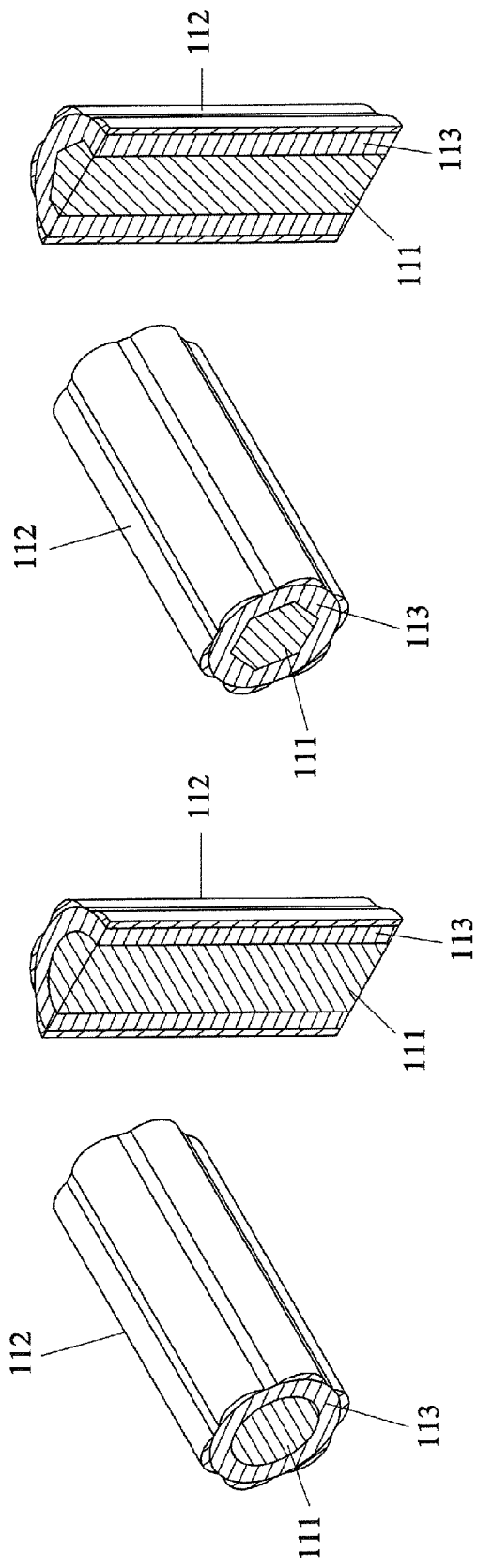
FIGS. 16A and 16B are illustrating schematic diagrams of a single filament used in the bone connection material according to the embodiments of the present invention.

Refer to FIGS. 16A, 16B, and 17, the shell layer 112 is formed with a strip layer. In FIG. 17, the middle layer 113 is formed with a hexagonal layer. The purpose of strip configuration of shell layer 112 is to provide more fixation force between filaments and between filaments and bone. In these embodiments, the shell layer 112 is made of bioinert material, the core layer 111 is made of bioactive glass, collagen, hydroxylapatite (HA), or tricalcium phosphate (TCP), and the middle layer 113 is made of materials with Xray opacity. In a preferred embodiment, layers 111,112,113 of the multilayer filament can be integrated with each other, for example, in a fusion manner, so that the strength of the multilayer filament can be enhanced.

Please refer to FIG. 18, the bone connection material 1 may be made into a double-screw configuration according to implementation requirements. In FIG. 18A, it can be seen that the filaments 11 are fixed within the resin of the covering layer 20 and thus are provided within the bone connection material 1 with double-screw configuration. Continue to refer to FIG. 18B, it can be seen that filaments 11 are braided to form a woven filament structure. FIG. 18C is illustrating a section-enlarged view of the woven filament structure. Besides, at least one of the core layer 111 and shell layer 112 is made of materials with Xray opacity, such that the bone connection material 1 can be shown up on a Xray scan. Please note that the above embodiments are described for illustrative purpose only, and are not meant for limitations of the present invention. In other embodiments, the bone connection material 1 can be formed as a structure more than three layers, various shapes and various materials can be selectively used as each layer, while one of those layers is made of bioinert materials for maintaining the structure of the bone connection material 1, and it is enough for X ray scan that only one layer of the multilayer filament is made of materials with Xray opacity. For example, a single filament used in the bone connection material 1 is ten-layer filament, each layer can be respectively formed with a round, a hexagonal, or a strip layer, and each layer can be respectively made of bioactive materials (bioglass, collagen, hydroxylapatite (HA), tricalcium phosphate (TCP)), bioinert materials, or materials with Xray opacity, while at least one layer is made of materials with Xray opacity.

The present invention, however, can be designed according to the portion where it is installed and may use a material (such as the multilayer filament described above) that can be long retained in human body, so that there is no need to take the secondary operation and the burden of the patient can be reduced.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

We claim:

1. A bone connection material, comprising:
   an internal layer, which is formed by braiding a plurality of filaments,
   wherein a single filament is a multilayer filament, at least one layer of the multilayer filament is made of material with Xray opacity;
   wherein a plurality of coefficients of thermal expansion of layers of the multilayer filament is equal to each other or gradually lower in order from an inner layer to an outer layer; and
   wherein a plurality of the braided filaments comprises:
   a center filament shaft being provided straightly through a plurality of the braided filaments; and
   a plurality of braided filament shafts interlaced-knitted around the center filament shaft.

2. The bone connection material according to claim 1, further comprising a covering layer, which encloses the filaments of the internal layer.

3. The bone connection material according to claim 2, wherein the covering layer is made of a resin or biocompatible polymer.

4. The bone connection material of claim 3, wherein the resin is bioinert.

5. The bone connection material of claim 3, wherein the resin is biodegradable.

6. The bone connection material of claim 3, wherein the resin is thermoplastic.

7. The bone connection material of claim 3, wherein the resin is thermosetting.

8. The bone connection material according to claim 2, wherein the covering layer further comprises collagen, hydroxylapatite (HA), or tricalcium phosphate (TCP).

9. The bone connection material of claim 1, wherein the multilayer filament includes a core layer and a shell layer, the shell layer encloses a circumferential surface of the core layer, or the multilayer filament includes a core layer, a middle layer, and a shell layer, the middle layer encloses a circumferential surface of the core layer, the shell layer encloses a circumferential surface of the middle layer.

10. The bone connection material of claim 9, wherein an outer surface of the shell layer has a punctate coating.

11. The bone connection material of claim 1, wherein at least one layer of the multilayer filament is made of bioinert material, and at least one layer of the multilayer filament is made of bioactive material.

12. The bone connection material of claim 11, wherein the bioactive material is bioglass, collagen, hydroxylapatite (HA), or tricalcium phosphate (TCP).

13. The bone connection material of claim 1, wherein each layer of the multilayer filament is formed with a round, a hexagonal, or a strip layer.

14. The bone connection material of claim 1, wherein layers of the multilayer filament are integrated with each other.

* * * * *